United States Patent [19]
Defauw

[11] Patent Number: 5,292,737
[45] Date of Patent: Mar. 8, 1994

[54] N,N'-BIS(SULFONAMIDO)-2-AMINO-4-IMINONAPHTHALEN-1-ONES AND N,N'-BIS(AMIDO)-2-AMINO-4-IMINONAPHTHALEN-1-ONES

[75] Inventor: Jean M. Defauw, Durham, N.C.

[73] Assignee: Sphinx Pharmaceuticals Corporation, Durham, N.C.

[21] Appl. No.: 965,354

[22] Filed: Oct. 23, 1992

[51] Int. Cl.$^5$ .................. A61K 31/50; A61K 31/505; A61K 31/44; C07D 237/08; C07D 401/12; C07D 261/08; C07D 239/24

[52] U.S. Cl. ........................ 514/247; 514/252; 514/256; 514/259; 514/260; 514/269; 514/272; 514/275; 514/332; 514/338; 514/339; 514/340; 514/341; 514/342; 514/343; 514/361; 514/378; 514/380; 514/603; 514/616; 544/224; 544/238; 544/239; 544/240; 544/241; 544/295; 544/298; 544/322; 544/333; 544/334; 544/335; 544/283; 544/284; 546/255; 546/271; 546/272; 546/276; 546/278; 546/283; 546/284; 548/243; 548/244; 548/245; 548/246; 548/247; 548/128; 548/129; 564/86; 564/155

[58] Field of Search .......... 548/243, 244, 245, 246, 548/247, 128, 129; 514/378, 380, 361, 247, 252, 256, 269, 272, 275, 259, 260, 603, 616, 332, 338, 339, 340, 341, 342, 343; 544/238, 239, 240, 241, 224, 295, 298, 322, 333, 334, 335, 283, 284; 564/86, 155; 546/255, 271, 272, 276, 278, 283, 284

[56] References Cited

U.S. PATENT DOCUMENTS 4,816,450 3/1989 Bell et al. ..................... 514/25

FOREIGN PATENT DOCUMENTS 3827974 2/1990 Fed. Rep. of Germany .
WO91/08189 6/1991 PCT Int'l Appl. .

OTHER PUBLICATIONS

Castagna, et al., (1982), J. Biol. Chem. 257:7847.
Grunicke et al., (1989) Adv. Enzyme Regul. 28:201.
Tritton, et al., Cancer Cells 2:5-102 (1990).
Schachtele et al., (1988), Biochem. Biophy. Res. Comm. 151:542.
Hannun et al., (1987) J. Biol. Chem. 262:13620.
Yamada et al. (1988) Biochem. Pharmacol. 37:1161.
McIntyre et al., (1987) J. Biol. Chem. 262:15730.
Lambreth et al., (1988), J. Biol. Chem. 263:12616.
Pittet et al., (1987), J. Biol. Chem. 262:10072.
Gaudry et al., (1988), Immunology 63:715.
Wilson, et al., (1986), J. Biol. Chem. 261:12616.
Fujita et al., (1986), Biochem. Pharmacol. 35:455.
Berkow et al., (1987), J. Leukoc. Biol. 41:441.
Salzer et al., (1987), Biochem. Biophys. Res. Commun. 148:787.
Kramer et al., (1989), J. Biol. Chem. 262:5876.
Dewald et al., (1989) Biochem. J. 264:879.
Cheng, C. C., (1974), J. Pharm. Sci. 63(2):307-310.
Winterbottom, (1940), J. Am. Chem. Soc. 62:160.
Fossbinder et al., (1939), J. Am. Chem. Soc. 61:2032.
Adams et al., (1959), J. Chem. Soc. 3061.
Leitch et al., (1945), Can. J. Res. 23B:139.
Lherer et al., (1981), J. Clinical Invest. 68:1314.
Roberts et al., (1982), J. Immunological Methods 49:193.
Venuti, M., et al., (1988) J. Med. Chem. 31:2132-2136.

Primary Examiner—Mary C. Lee
Assistant Examiner—Joseph K. McKane
Attorney, Agent, or Firm—Woodcock Washburn Kurtz Mackiewicz & Norris

[57] ABSTRACT

N,N'-Bis(sulfonamido)-2-amino-4-iminonaphthalen-1-ones and N,N'-Bis(amido)-2-amino-4-iminonaphthalen-1-ones are disclosed. Methods of inhibiting protein kinase C activity which comprises contacting protein kinase C with an effective amount of an N,N'-Bis(sulfonamido)-2-amino-4-iminonaphthalen-1-one or an N,N'-Bis(amido)-2-amino-4-iminonaphthalen-1-one are disclosed. Methods of treating an animal that is suspected of suffering from inflammatory, cardiovascular and/or neoplastic diseases which comprises administering an effective amount of an N,N'-Bis(sulfonamido)-2-amino-4-iminonaphthalen-1-one or an N,N'-Bis(amido)-2-amino-4-iminonaphthalen-1-one are disclosed.

26 Claims, No Drawings

N,N'-BIS(SULFONAMIDO)-2-AMINO-4-IMINONAPHTHALEN-1-ONES AND N,N'-BIS(AMIDO)-2-AMINO-4-IMINONAPHTHALEN-1-ONES

FIELD OF THE INVENTION

The present invention relates to the field of treatments for inflammatory, cardiovascular and neoplastic diseases. More particularly, the present invention relates to novel N,N'-Bis(sulfonamido)-2-amino-4-iminonaphthalen-1-ones and N,N'-Bis(amido)-2-amino-4-iminonaphthalen-1-ones which inhibit the enzyme protein kinase C.

BACKGROUND OF THE INVENTION

Protein kinase C (PKC) is a family of calcium- and phospholipid-dependent serine/threonine-specific protein kinases which play an important role in cellular growth control, regulation, and differentiation. Protein kinase C is activated by diacylglycerol (DAG), a neutral lipid, and when activated will transfer the g-phosphate of MgATP to a serine or threonine residue on a substrate protein. The mechanisms of protein kinase C action have been described in U.S. Pat. No. 4,816,450 issued Mar. 28, 1989 to Bell et al., which is incorporated herein by reference.

The activation of protein kinase C has been implicated in several human disease processes, including cancer tumors, inflammation and reperfusion injury. Accordingly, protein kinase C is a target for therapeutic agents useful in treating these conditions.

Cancer is a disease characterized in part by uncontrolled cell growth. Protein kinase C is directly involved in cellular growth control and is believed to be involved in tumor formation. Protein kinase C is fundamental to the processes involved in tumorigenicity, since it is the major high-affinity receptor for endogenous cellular DAGs as well as for several classes of tumor promoters. These tumor promoters also stimulate protein kinase C catalysis. Castagna et al., (1982) J. Biol. Chem. 257:7847, reported direct activation of protein kinase C by tumor promoting phorbol esters.

Protein kinase C is the major, if not exclusive, intracellular receptor of phorbol esters, which are very potent tumor promoters. Phorbol esters and other tumor promoters bind to and activate protein kinase C. Since DAG and phorbol esters interact at the same site, DAGs have been suggested to be the "endogenous phorbol esters", analogous to the opiate receptor where the conservation of a high affinity receptor implied the existence of an endogenous analogue. DAG has been shown to increase the affinity of protein kinase C for $Ca^{+2}$ and phospholipid and thus activates protein kinase C at cellular levels of these essential cofactors. Extracellular signals including hormones, growth factors, and neurotransmitters are known to stimulate phosphatidylinositol turnover resulting in the generation of $IP_3$ and DAG.

Structures of 40 distinct oncogenes of viral and cellular origin have revealed that oncogenes encode altered forms of normal cellular proteins. Several of the gene products appear related to growth factors or other elements involved in transmembrane signalling. These oncogene products appear to function by altering the level of critical second messengers. Cells transformed with the oncogenes ras, sis, erbB, abl, and src have been shown to contain elevated levels of DAG which is then believed to activate protein kinase C. Studies on ras transformed cells have shown protein kinase C activation to be concomitant with elevation of DAG.

Phorbol esters, such as phorbol myristate acetate (PMA), have complex effects on cells including effects on membrane function, mitogenesis, differentiation, and gene expression. Synthetic DAGs mimic many of the effects of PMA in vitro and inhibitors of protein kinase C have been shown to block PMA-induced effects on cells. Thus, protein kinase C may mediate the actions of certain oncogenes, such as ras, which cause intracellular increases in DAG and concomitant increases in protein kinase C. In addition, activation of protein kinase C leads to the expression of c-myc, c-fos, c-cis, c-fms, nuclear protooncogenes which are important in cell transformation. Overexpression of protein kinase C in NIH 3T3 cells causes altered growth regulation and enhanced tumorigenicity and in rat fibroblasts leads to anchorage-independent growth in soft agar. Overexpression of protein kinase C in these cells resulted in tumor formation in animals receiving transplanted cells.

Several studies have shown increased expression of protein kinase C in certain tumor types such as breast and lung carcinomas. Activated protein kinase C has also been detected in human colon carcinomas although increased expression at the gene level was not seen. Topoisomerases are directly modulated by protein kinase C as substrates for the enzyme.

Protein kinase C inhibitors have been reported to potentiate the antitumor activity of chemotherapeutic agents such as cis-platin both in vitro and in vivo (Grunicke et al. (1989) Adv. Enzyme Regul. 28:201; and German Offenlegungsschrift DE 3827974). In addition, it has been suggested that protein kinase C would be a potential target for therapeutic design because of its central role in cell growth (Tritton, T. R. and Hickman, J. A. Cancer Cells 2:5–102 (1990).

Inflammation and reperfusion injury, particularly pertaining to cardiac injury, are common conditions for which there exists no definitive treatment despite extensive research. Appropriate treatments for these conditions are needed.

Protein kinase C inhibitors have been demonstrated to block platelet aggregation and release of neutrophil activating agents such as platelet activating factor (PAF) (Schachtele et al. (1988) Biochem Biophy. Res. Commun. 151:542; Hannun et al (1987) J. Biol. Chem. 262:13620; Yamada et al. (1988) Biochem. Pharmacol. 37:1161). Protein kinase C inhibitors have also been shown to inhibit neutrophil activation, and chemotactic migration (McIntyre et al. (1987) J. Biol Chem. 262:15730; Lambreth et al. (1988) J. Biol. Chem. 263:3818; Pittet et al. (1987) J. Biol. Chem. 262:10072; and Gaudry et al. (1988) Immunology 63:715), as well as neutrophil degranulation and release of proteolytic enzymes and reactive oxygen intermediates (Wilson et al. (1986) J. Biol. Chem. 26:12616; Fujita et al. (1986) Biochem. Pharmacol. 35:4555; Berkow et al. (1987) J. Leukoc., Biol. 41:441; Salzer et al. (1987) Biochem. Biophys. Res. Commun. 148:747; Kramer et al. (1989) J. Biol. Chem. 262:5876; and Dewald et al. (1989) Biochem. J. 264:879).

Thus, inhibitors of protein kinase C have the capability of blocking all three of the most significant mechanisms of pathogenesis associated with myocardial reperfusion injury. Protein kinase C is, accordingly, a drug target for therapeutic agents. Additionally, the inhibitory effect of protein kinase C inhibitors on keratinocytes, and on the oxidative burst in neutrophils, provides an anti-inflammatory effect.

German Offenlegungsschrift DE 3827974 A1 discloses therapeutic preparations comprising a protein kinase C inhibitor in combination with a lipid, a lipid analogue, a cytostatic agent or phospholipase inhibitor which are useful for cancer therapy.

Cheng, C.C., (1974) J. Pharm. Sci. 63(2)307-310, disclose quinone imines as having antimalarial activity.

SUMMARY OF THE INVENTION

The present invention relates to compounds having the following formula:

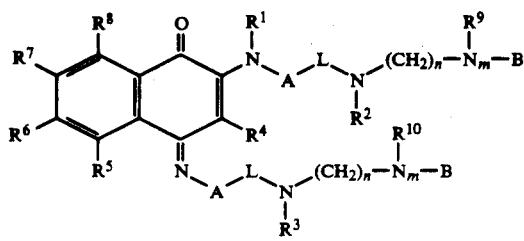

wherein:
  A is: a 5, 6 or 7 membered monocyclic, fused bicyclic or fused tricyclic aromatic or heterocyclic ring system; or is a $C_2$-$C_4$ conjugated alkenyl;
  L is: $SO_2$ or CO;
  $R^1$, $R^2$, and $R^3$ are, each independently: hydrogen, alkyl, aryl, alkylaryl, arylalkyl or cycloalkyl;
  $R^4$, $R^5$, $R^6$, $R^7$ and $R^8$ are, independently: hydrogen, alkyl, aryl, alkylaryl, arylalkyl, halogen, nitro, amino, acylamino, hydroxy, carboxyl, alkoxy, aryloxy, thioalkoxy, alkylthio, arylthio, or a fused aromatic ring;
  B is: hydrogen, aryl, $C_3$-$C_8$ cycloalkyl; $C_1$-$C_{20}$ alkyl, $C_2$-$C_{20}$ alkenyl, amidino, $C_2$-$C_{20}$ alkynyl, acyl or substituted thereof; or pyrrolyl, imidazolyl, triazolyl, tetrazolyl, furanyl, thiophenyl, isoxazolyl, isothiazolyl, oxazolyl, 1,2,4-thiadiazolyl, pyridazinyl, pyrimidinyl, pyrazinyl, quinoxalinyl, quinolinyl or isoquinolinyl, wherein all rings may be substituted;
  m is: 0-1; and
  n is: 0-6;
  wherein if m is 1 then $R^9$ and $R^{10}$ are, independently: hydrogen, alkyl, aryl, alkylaryl, arylalkyl or cycloalkyl.

Additionally, the present invention relates to pharmaceutically acceptable salts of the above compounds.

The present invention relates to a method of inhibiting protein kinase C activity which comprises contacting said protein kinase C with an effective amount of an N,N'-Bis(sulfonamido)-2-amino-4-iminonaphthalen-1-one or an N,N'-Bis(amido)-2-amino-4-iminonaphthalen-1-one. The present invention relates to a method of treating an animal that is suffering from inflammatory, cardiovascular and/or neoplastic diseases by administering an effective amount of an N,N'-Bis(sulfonamido)-2-amino-4-iminonaphthalen-1-one or an N,N'-Bis-(amido)-2-amino-4-iminonaphthalen-1-one.

DETAILED DESCRIPTION OF PREFERRED EMBODIMENTS

The present invention relates to N,N'-Bis(sulfonamido)--2-amino-4-iminonaphthalen-1-ones, N,N'-Bis(amido)-2-amino-4--iminonaphthalen-1-one, and their pharmaceutically acceptable salts, respectively. Compounds according to the present invention have been shown to inhibit protein kinase C. PCK inhibitors are useful in the treatment of cancer, inflammatory and reperfusion injury through their antiproliferative and anti-inflammatory activities in human neutrophils, human keratinocytes, and human tumor cells.

The present invention relates to a method of inhibiting protein kinase C activity which comprises contacting said protein kinase C with an effective amount of an N,N'-Bis(sulfonamido)-2-amino-4-iminonaphthalen-1-one, an N,N'-Bis(amido)-2-amino-4-iminonaphthalen-1-one or a pharmaceutically acceptable salt thereof. Protein kinase C inhibitors are useful as anti-inflammatory, antitumor, and reperfusion injury agents through their antiproliferative and anti-inflammatory activities in human neutrophils, human keratinocytes, and human tumor cells. The present invention relates to a method of treating a animal suffering from inflammatory, cardiovascular and/or neoplastic diseases by administering an amount of an N,N'-Bis(sulfonamido)-2-amino-4-iminonaphthalen-1-one, an N,N'-Bis(amido)-2-amino-4-iminonaphthalen-1-one or a pharmaceutically acceptable salt thereof.

The method of the present invention comprises inhibiting protein kinase C activity by contacting protein kinase C with an effective amount of an N,N,-Bis(sulfonamido)-2-amino--4-iminonaphthalen-1-one or N,N'-Bis(amido)-2-amino-4-iminaphthalen-1-one. N,N'-Bis(sulfonamido)-2-amino-4-iminonaphthalen-1-ones and N,N'-Bis(amido)-2-amino-4-iminonaphthalen-1-one have been discovered to inhibit the activity of protein kinase C. Exposure of cells in vitro to N,N'-Bis(sulfonamido)-2-amino-4-iminonaphthalen-1-ones or N,N'-Bis(amido)-2-amino-4-iminonaphthalen-1-ones results in the inhibition of PKC activity Inhibition of PKC activity in cells impedes cellular activities associated with several disease conditions.

The method that is the present invention is useful in the treatment of diseases which involve cellular growth, regulation and differentiation such as inflammatory, cardiovascular and neoplastic diseases. PKC activity is associated with disease conditions such as cancer, inflammation and reperfusion injury. Accordingly, the present invention relates to a method of treating a mammal suffering from cancer, inflammation such as the type associated with arthritis or reperfusion injury. The method comprises administering to the mammal, an effective amount of an N,N'-Bis(sulfonamido)-2-amino-4-iminonaphthalen-1-one, an N,N'-Bis(amido)-2-amino-4-iminonapthalen-1-one or a pharmaceutically acceptable salt thereof which inhibits PKC activity.

PKC phosphorylates certain molecules, referred to herein as phosphorylation acceptor molecules. In order to identify compounds that inhibit PKC activity, an assay is performed in which radiolabelled ATP is combined with a phosphorylation acceptor molecule in the presence of PKC and either an N,N'-Bis(sulfonamido)-2-amino-4-iminonaphthalen-1-one or an N,N',-Bis-(amido)-2-amino-4-iminonaphthalen-1-one PKC inhibitor-candidate compound (hereinafter referred to as a "test compound"). Various amounts of test compound are used to determine the level of inhibitory activity that a particular compound possesses. As a control, radiolabelled ATP, phosphorylation acceptor molecule and PKC are combined without test compound. Assay conditions such as pH, salt and cofactor conditions are maintained similar to physiological levels in order to duplicate in vivo conditions. In the assay, if PKC is active, the phosphorylation receptor molecule will be phosphorylated, gaining a radiolabelled phosphorus atom. Thus, the inhibitory activity of the test compound can be determined by incubating PKC, $^{32}$P-ATP, phosphorylation receptor molecule and test compound and then measuring the level of phosphorylation activity by measuring the level of radioactive phosphorus present in the phosphorylation receptor molecule.

To determine the selectivity of PKC inhibitory activity, test compounds are investigated for cAMP dependent protein kinase (PKA) inhibitory activity As in the PKC assay, the level of inhibitory activity is determined by measuring the level of phosphorylation of a phosphorylation acceptor molecule incubated with radiolabelled ATP and PKA. Preferred PKC inhibitors are selective inhibitors and do not effect the activity of PKA.

In order to investigate the effect that the N,N'-Bis(-sulfonamido)-2-amino-4-iminonaphthalen-1-one or N,N'-Bis(amido)-2-amino-4-iminonaphthalen-1-one PKC inhibitors of the present invention have on cell growth and activity, assays are performed to determine human tumor cell growth inhibition, human keratinocyte inhibition and neutrophil superoxide anion release. Briefly, a human tumor cell growth inhibition assay measures the growth of tumor cells in the presence PKC inhibitors by measuring the incorporation of radiolabelled amino acid in cells. The human keratinocyte inhibition assay measures the proliferation of human epidermal keratinocytes in the same manner as tumor cell growth is measured. Hyperproliferation of keratinocytes is symptomatic of many disease conditions associated with inflammation. The neutrophil superoxide anion release assay measures a PKC inhibitors ability to block the PMA-induced effects on cells. The ability of the PKC inhibitors to affect superoxide release by PMA stimulated neutrophils is determined by measuring cytochrome C reduction. Cytochrome C is measured by measuring optical density.

The compounds of the present invention, referred to herein as N,N'-Bis(sulfonamido)-2-amino-4-iminonaphthalen-1-ones and N,N'-Bis(amido)-2-amino-4-iminonaphthalen-1-ones, can be expressed by the formula:

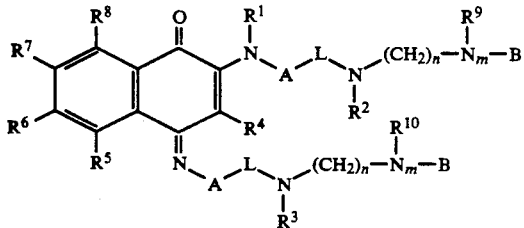

wherein:
A is: a 5, 6 or 7 membered monocyclic, fused bicyclic or fused tricyclic aromatic or heterocyclic ring system; or is a $C_2$-$C_{14}$ conjugated alkenyl;
L is: $SO_2$ or CO;
$R^1$-$R^3$ are each, independently: hydrogen, alkyl, aryl, alkylaryl, arylalkyl or cycloalkyl;
$R^4$-$R^8$ are each, independently: hydrogen, alkyl, aryl, alkylaryl, arylalkyl, halogen, nitro, amino, acyl-amino, hydroxy, carboxyl, alkoxy, aryloxy, thioalkoxyl, alkylthio, arylthio or a fused aromatic ring;
B is: hydrogen, aryl, $C_3$-$C_8$ cycloalkyl, $C_1$-$C_{20}$ alkyl, $C_2$-$C_{20}$ alkenyl, amidino, $C_2$-$C_{20}$ alkynyl, acyl or substituted thereof; or pyrrolyl, imidazolyl, triazolyl, tetrazolyl, furanyl, thiophenyl, isoxazolyl, isothiazolyl, oxazolyl, 1,2,4-thiadiazolyl, pyridazinyl, pyrimidinyl, pyrazinyl, quinoxalinyl, quinolinyl or isoquinolinyl, wherein all rings may be substituted;
m is: 0-1; and,
n is: 0-6;
wherein if n is 1, then
$R^9$ and $R^{10}$ are each, independently: hydrogen, alkyl, aryl, alkylaryl, arylalkyl or cycloalkyl.

Pharmaceutically acceptable salts of these compounds may be used in the method that is the present invention.

Compounds according to the present invention can have at position A: a 5, 6 or 7 membered monocyclic, fused bicyclic or fused tricyclic aromatic or heterocyclic ring system; or a $C_2$-$C_4$ conjugated alkenyl. It is preferred that A is: p-phenyl, m-phenyl, o-phenyl, 4-methyl-3-phenyl, 2-chloro-4-phenyl, 2-chloro-3-thiophenyl, 2-pyridinyl, 2,4,5-thiadiadiazolyl, ethenyl, 1,3-butadienyl, naphthyl, 2-quinolinoyl 6-quinolinoyl, or 3-(6-methylphenyl). A is more preferrably: p-phenyl; m-phenyl; or 3-(6-methylphenyl).

Compounds according to the present invention can have at position L: $SO_2$ or CO.

Compounds according to the present invention can have, independently, at positions $R^1$, $R^2$ and $R^3$: hydrogen, alkyl, alkenyl, alkynyl, aryl, alkylaryl, arylalkyl or cycloalkyl. It is preferred that $R^1$, $R^2$ and $R^3$ are hydrogen or lower aliphatic, i.e , $C_1$-$C_{20}$ or aromatic groups. It is most preferred that $R_1$, $R^2$ and $R^3$ are hydrogen.

Compounds according to the present invention can have, independently, at positions $R^4$, $R^5$, $R^6$, $R^7$ and $R^8$: hydrogen, alkyl, aryl, alkylaryl, arylalkyl, halogen, nitro, amino, acylamino, hydroxy, carboxyl, alkoxy, aryloxy, thioalkoxyl, alkylthio, arylthio or a fused aromatic ring. It is preferred that $R^4$, $R^5$, $R^6$, $R^7$ and $R^8$ are hydrogen or lower aliphatic, i.e. $C_1$-$C_{20}$ or aromatic groups. It is most preferred that $R^4$, $R^5$, $R^6$, $R^7$ and $R^8$ are hydrogen.

Compounds according to the present invention can have at position B: hydrogen, aryl, $C_3$-$C_8$ cycloalkyl; $C_1$-$C_{20}$ alkyl, $C_2$-$C_{20}$ alkenyl, amidino, $C_2$-$C_{20}$ alkynyl, acyl or sustituted thereof; or pyrrolyl, imidazolyl, triazolyl, tetrazolyl, furanyl, thiophenyl, isoxazolyl, isothiazolyl, oxazolyl, 1,2,4-thiadiazolyl, pyridazinyl, pyrimidinyl, pyrazinyl, quinoxalinyl, quinolinyl or isoquinolinyl, wherein all rings may be substituted. It is preferred that B is: 3-(5-methylisoxazolyl); 5-(3,4-dimethylisoxazolyl); 2-(4,6-dimethylpyrimidinyl); 4-(2,6-dimethylpyrimidinyl);2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-chloropyridazinyl); methoxypyridazinyl); 2-pyrimidinyl; 3-(6-chloropyridazinyl); 2-quinoxalinoyl; hexadecyl; amidino; 2-(5-nitropyridinyl); hydrogen; 5-(1,3 dimethoxyphenyl); 2-(4,6 dimethylpyridinyl); or 3-(2-carbomethoxythiophenyl). B is more preferrably: 3-(5-methylisoxazolyl); 2-(4,6-dimethylpyrimidinyl); 4-(2,6-dimethoxypyrimidinyl); 2-(5-methoxypyrimidinyl);2-pyridinyl; 3-(6-methoxypyridazinyl); 2-quinoxalinoyl; 2-(5-nitropyridinyl); 2-(4-6 dimethylpyridinyl); or 5-(1,3 dimethoxyphenyl). B is most preferrably: 2-(4,6-dimethylpyrimidinyl); 2-pyridinyl; 2-quinoxalinoyl; 2-(5-nitropyridinyl); 2-(4-6 dimethylpyridinyl); or 5-(1,3 dimethoxyphenyl).

In compounds according to the present invention, m is 0-1.

Compounds according to the present invention in which m is 1, can have, independently, at $R^9$ and $R^{10}$: hydrogen, alkyl, alkenyl, alkynyl, aryl, alkylaryl, arylalkyl or cycloalkyl. It is preferred that $R^9$ and $R^{10}$ are: hydrogen, lower aliphatic, i.e., $C_1$-$C_{20}$; lower cycloalkyl groups, i.e., $C_3$-$C_8$; or aromatic groups. It is most preferred that $R^9$ and $R^{10}$ are hydrogen.

In compounds according to the present invention, n is 0-6. It is preferred that n is 0-3. It is most preferred that n is 0-2.

Pharmaceutically acceptable salts of these compounds may be used according to the present invention. One having ordinary skill in the art could readily appreciate what salts would be appropriate. Pharmaceutically acceptable salts include, but are not limited to those that include sodium, tromethamine, potassium, calcium, zinc, lithium, magnesium, aluminum, diethanolmine, ethylenediamine, meglumine and acetic acid. Preferred salts include sodium and potassium. The most preferred salts include sodium.

In certain preferred compounds of the present invention:

$R^1$, $R^2$, $R^3$, $R^4$, $R^5$, $R^6$, $R^7$ and $R^8$ are each hydrogen;
A is phenyl, 4-methyl-3-phenyl, 2-chloro-4-phenyl, 2-chloro-3-thiophenyl, 2-pyridinyl, 2,4,5-thiadiadiazolyl, ethenyl, 1,3-butadienyl, naphthyl, 2-quinolinoyl, 6-quinolinoyl, or 3-(6-methylphenyl);
L is $SO_2$ or CO;
B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 3-(6-chloropyridazinyl); 2-quinoxalinoyl; hexadecyl; amidino; 2-(5-nitropyridinyl); hydrogen; 5-(1,3 dimethoxyphenyl); 2-(4,6 dimethylpyridinyl); or 3-(2-carbomethoxythiophenyl);
m is 0-1; and
n is 0-3;
wherein when m is 1, $R^9$ and $R^{10}$ are each hydrogen.

In certain preferred compounds of the present invention:

$R^1$, $R^2$, $R^3$, $R^4R^5$, $R^6$, $R^7$ and $R^8$ are each hydrogen;
A is p-phenyl; m-phenyl; or 3-(6-methylphenyl);
L is $SO_2$ or CO;
B is 3-(5-methylisoxazolyl); 2-(4,6-dimethylpyrimidinyl); 4-(2,6-dimethoxypyrimidinyl); 2-(5-methoxypyrimidinyl); 2-pyridinyl; 3-(6-methoxypyridazinyl); 2-quinoxalinoyl; 2-(5-nitropyridinyl); 2-(4-6 dimethylpyridinyl); or 5-(1,3 dimethoxyphenyl);
m is 0-1; and
n is 0-2;
wherein when m is 1, $R^9$ and $R^{10}$ are each hydrogen.

In certain preferred compounds of the present invention:

$R^1$, $R^2$, $R^3$, $R^4$, $R^5$, $R^6$, $R^7$ and $R^8$ are each hydrogen;
A is p-phenyl; m-phenyl; or 3-(6-methylphenyl);
L is $SO_2$ or CO;
B is 2-(4,6-dimethylpyrimidinyl); 2-pyridinyl; 2-quinoxalinoyl; 2-(5-nitropyridinyl); 2-(4-6-dimethylpyridinyl); or 5-(1,3 dimethoxyphenyl);
m is 0-1; and
n is 0-2;
wherein when m is 1, $R^9$ and $R^{10}$ are each hydrogen.

Compounds of the present invention may be synthesized from readily available starting materials by standard techniques such as by following the basic synthesis set out below. Other synthesis schemes may also be followed.

Reaction of commercially available 1,2-naphthoquinone-4-sulfonic acid, potassium salt (Compound I) in anhydrous dimethyl sulfoxide with either a sulfonomide or an amide (Compound II) at room temperature gives a mixture of products (Compound III), (Compound IV), and (Compound V). However, the desired products, the N,N'-Bis(sulfonamido)-2-amino-4-iminonaphthalen-1-ones or N,N'-Bis(sulfonamido)-2-amino-4-iminonaphthalen-1-ones, are the major product if the reaction mixture is allowed to stir for 1 to 7 hours.

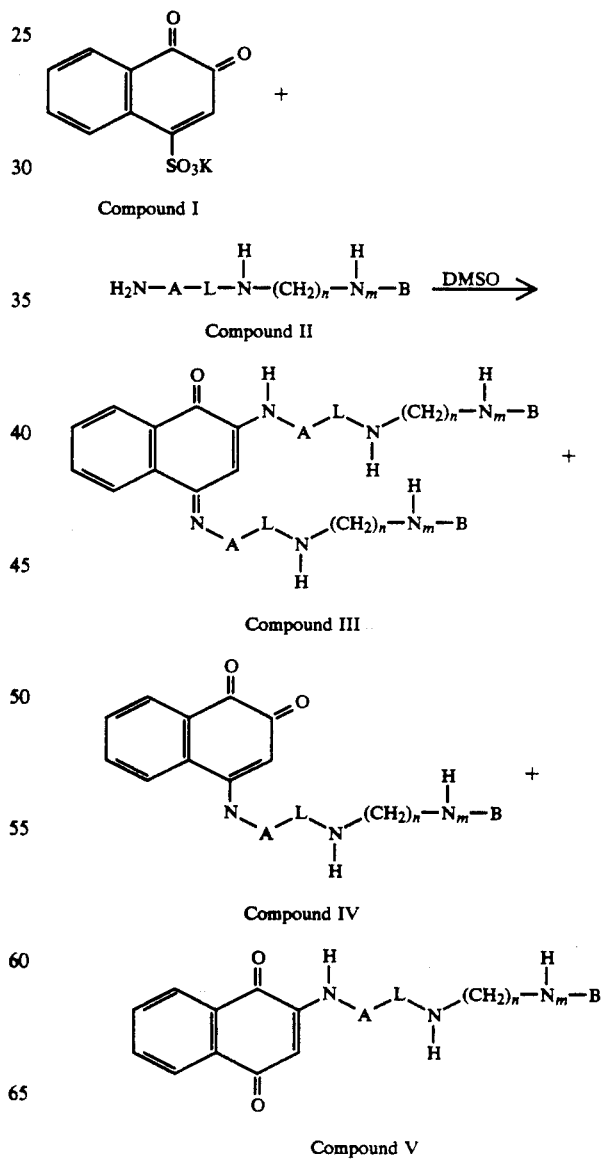

Compound I

Compound II

Compound III

Compound IV

Compound V

The sulfonamides and amides (Compound II) were either commercially available or prepared according to the literature (see for example: Winterbottom (1940) J. Am. Chem. Soc. 62:160; Fossbinder et al, (1939) J. Am. Chem. Soc. 61:2032; Adams et al, (1959) J. Chem. Soc. 3061; and Leitch et al, (1945) Can. J. Res. 23B:139).

Sodium salts of compounds in which L is $SO_2$ (Compound VI) were prepared upon treatment of N,N'-Bis(sulfonamido)-2-amino--4-iminonaphthalen-1-ones (Compound III) in methanol with solutions of sodium hydroxide in distilled water.

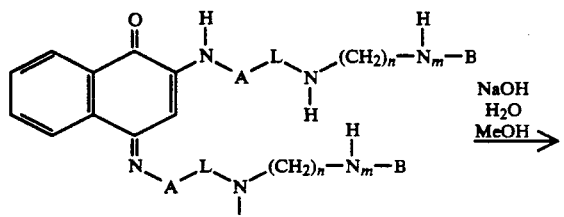

Compound III

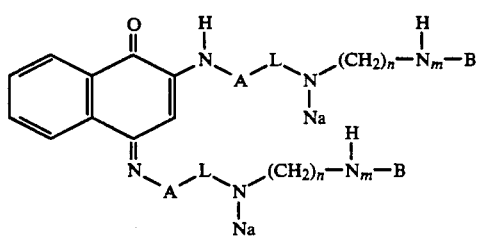

Compound VI

Compounds according to the present invention inhibit the activity of PKC in cells. The range of amounts of inhibitory compound that a cell can be exposed to that is effective for inhibiting PKC activity can be determined by one having ordinary skill in the art.

By inhibiting PKC activity, N,N'-Bis(sulfonamido)--2-amino-4-iminonaphthalen-1-ones and N,N'-Bis(amido)-2--amino-4-iminonaphthalen-1-ones are useful in the treatment of disease conditions in which control of cellular growth, regulation and/or differentiation is desirable. Effective amounts of N,N'-Bis(sulfonamido)-2-amino-4-iminonaphthalen-1-ones or N,N'-Bis(amido)-2-amino-4-iminonaphthalen-1-ones can be administered to mammals who are suffering from inflammatory, cardiovascular or neoplastic diseases, particularly inflammation, reperfusion injury and cancer, in order to counter the disease at the cellular level.

Pharmaceutical preparations incorporating compounds according to the present invention can be used to block PKC activity related to abnormal or undesirable cellular events and activity including tumorogeneis and cellular activity related to inflammation and reperfusion injury. Treatment of disorders and disease conditions can be performed by administration of effective amounts of pharmaceutical preparation that comprise compounds according to the present invention. Compounds can be formulated for human and animal prophylactic and therapeutic applications by those having ordinary skill in the art. The range of amounts of a compound to be administered to mammals, particularly humans, to be effective in inflammatory, tumor or reperfusion injury therapy can be determined by those having ordinary skill in the art.

The compounds and pharmaceutical compositions of the invention may be administered by any method that produces contact of the active ingredient with the agent's site of action in the body of a mammal or in a body fluid or tissue. These methods include but not limited to oral, topical, hypodermal, intravenous, intramuscular and intraparenteral methods of administration. The compounds may be administered singly or in combination with other compounds of the invention, other pharmaceutical compounds such as chemotherapeutic compounds, or in conjunction with therapies such as radiation treatment. The compounds of the invention are preferably administered with a pharmaceutically acceptable carrier selected on the basis of the selected route of administration and standard pharmaceutical practice.

The compounds of the invention are administered to mammals, preferably humans, in therapeutically effective amounts which are effective to inhibit protein kinase C, to inhibit tumor cell growth, inhibit inflammation of tissue, inhibit keratinocyte cell proliferation, inhibit oxidative burst from neutrophils or inhibit platelet aggregation. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a compound of the invention will be in the range of from about 1 µg to about 100 mg per kg of body weight, preferably from about 1 µg to about 1 mg per kg body weight, and more preferably from about 10 µg to about 1 mg per kg per day, and preferably administered in a single dosage or in divided dosages. Persons of ordinary skill will be able to determine dosage forms and amounts with only routine experimentation based upon the considerations of this invention.

The compounds of the invention may be administered as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds of the invention may be formulated into dosage forms according to standard practices in the field of pharmaceutical preparations See *Remington's Pharmaceutical Sciences*, A. Osol, Mack Publishing Company, Easton, Pa.

Compounds of the invention may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, a compound of the invention may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound of the invention. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl-or propyl-paraben, and chlorbutanol.

The following nonlimiting Examples illustrate the preferred methods for preparing the compounds for use in the method of the present invention and the data demonstrating PKC inhibitory activity of the Compounds used in the present invention.

EXAMPLES

EXAMPLE 1

Preferred compounds according to the present invention have the formula:

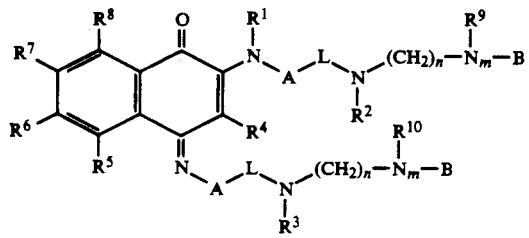

wherein
$R^1$, $R^2$, $R^3$, $R^4$, $R^5$, $R^6$, $R^7$ and $R^8$ are each hydrogen; and:

in compounds 3a and 6a, A is p-phenyl, L is $SO_2$, m is 0, n is 0 and B is 3-(5-methylisoxazolyl);

in compounds 3b and 6b, A is p-phenyl, L is $SO_2$, m is 0, n is 0 and B is 5-(3,4-dimethylisoxazolyl);

in compounds 3c and 6c; A is p-phenyl, L is $SO_2$, m is 0, n is 0 and B is 2-(4,6-dimethylpyrimidinyl);

in compounds 3d and 6d; A is p-phenyl, L is $SO_2$, m is 0, n is 0 and B is 4-(2,6-dimethylpyrimidinyl);

in compounds 3e and 6e; A is p-phenyl, L is $SO_2$, m is 0, n is 0 and B is 2-(5-methyl-1,3,4-thiadiazolyl);

in compounds 3f and 6f; A is p-phenyl, L is $SO_2$, m is 0, n is 0 and B is 2-(4-methylpyrimidinyl);

in compounds 3g and 6g: A is p-phenyl, L is $SO_2$, m is 0, n is 0 and B is 4-(2,6-dimethoxypyrimidinyl);

in compounds 3h and 6h, A is p-phenyl, L is $SO_2$, m is 0, n is 0 and B is 2-(5-methoxypyrimidinyl);

in compounds 3i and 6i, A is p-phenyl, L is $SO_2$, m is 0, n is 0 and B is 2-pyridinyl;

in compounds 3j and 6, A is p-phenyl, L is $SO_2$, m is 0, n is 0 and B is 3-(6-methoxypyridazinyl);

in compounds 3k and 6k, A is p-phenyl, L is $SO_2$, m is 0, n is 0 and B is 2-pyrimidinyl;

in compounds 3l and 6l, A is p-phenyl, L is $SO_2$, m is 0, n is 0 and B is 3-(6-chloropyridazinyl);

in compounds 3m and 6m, A is p-phenyl, L is $SO_2$, m is 0, n is 0 and B is 2-quinoxalinoyl;

in compounds 3n and 6n, A is p-phenyl, L is $SO_2$, m is 0, n is 1 and B is 2-pyridinyl;

in compounds 3o and 6o, A is p-phenyl, L is $SO_2$, m is 0, n is 0 and B is hexadecyl;

in compound 3p, A is m-phenyl, L is $SO_2$, m is 0, n is 0 and B is 2-(4,6-dimethylpyrimidinyl);

in compound 3q, A is o-phenyl, L is $SO_2$, m is 0, n is 0 and B is 2-(4,6-dimethylpyrimidinyl);

in compound 3r, A is 4-methyl-3-phenyl, L is $SO_2$, m is 0, n is 0 and B is 2-(4,6-dimethylpyrimidinyl);

in compound 3s, A is 2-chloro-4-phenyl, L is $SO_2$, m is 0, n is 0 and B is 2-(4,6-dimethylpyrimidinyl);

in compound 3t, A is 2-chloro-3-thiophenyl, L is $SO_2$, m is 0, n is 0 and B is 2-(4,6-dimethylpyrimidinyl);

in compound 3u, A is 2-pyridinyl, L is $SO_2$, m is 0, n is 0 and B is 2-(4,6-dimethylpyrimidinyl);

in compound 3v, A is 2,4,5-thiadiazolyl, L is $SO_2$, m is 0, n is 0 and B is 2-(4,6-dimethylpyrimidinyl);

in compound 3w, A is ethenyl, L is $SO_2$, m is 0, n is 0 and B is 2-(4,6-dimethylpyrimidinyl);

in compound 3x, A is 1,3-butadienyl, L is $SO_2$, m is 0, n is 0 and B is 2-(4,6-dimethylpyrimidinyl);

in compound 3y, A is naphthyl, L is $SO_2$, m is 0, n is 0 and B is 2-(4,6-dimethylpyrimidinyl);

in compound 3z, A is 2-quinolinoyl, L is $SO_2$, m is 0, n is 0 and B is 2-(4,6-dimethylpyrimidinyl);

in compound 3aa, A is 6-quinolinoyl, L is $SO_2$, m is 0, n is 0 and B is 2-(4,6-dimethylpyrimidinyl).

in compound 3ab, A is p-phenyl, L is $SO_2$, m is 0, n is 0 and B is amidino;

in compound 3ac, A is p-phenyl, L is $SO_2$, m is 1, n is 2, B is 2-(5-nitropyridinyl), and $R^9$ and $R^{10}$ are each hydrogen;

in compound 3ad, A is p-phenyl, L is $SO_2$, m is 0, n is 0 and B is hydrogen;

in compounds 3ae and 6ae, A is m-phenyl, L is $SO_2$, m is 0, n is 0 and B is 2-(4-6 dimethylpyridinyl);

in compounds 3af and 6af, A is p-phenyl, L is $SO_2$, m is 0, n is 0 and B is 5-(l,3 dimethoxyphenyl)

in compounds 3ag and 6ag, A is 3-(6-methylphenyl), L is $SO_2$, m is 0, n is 0 and B is 2-(4-6 dimethylpyridinyl);

in compound 3ah, A is p-phenyl, L is CO, m is 0, n is 0 and B is 2-(4,6 dimethylpyridinyl)

in compound 3ai, A is p-phenyl, L is CO, m is 0, n is 0 and B is 2-(4,6 dimethylpyridinyl)

in compound 3aj, A is p-phenyl, L is $SO_2$, m is 0, n is 0 and B is 2-(4,6 dimethylpyridinyl)

in compound 3ak, A is p-phenyl, L is $SO_2$, m is 0, n is 0 and B is 3-(2-carbomethoxythiophenyl).

Table 1 provides a list of preferred compounds and Tables 2 lists information about compounds including salt type, recrystallization solvents and melting point.

TABLE 1

The following compounds are represented by the formula:

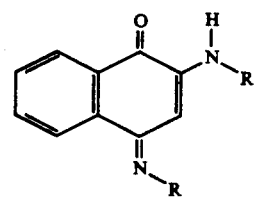

| Compound | R |
|---|---|
| 3a. | N-[3-(5-methylisoxazolyl)] p-benzenesulfonamido |
| 6a. | N-[3-(5-methylisoxazolyl)] p-benzenesulfonamido |
| 3b. | N-[5-(3,4-dimethylisoxazolyl)] p-benzenesulfonamido |
| 6b. | N-[5-(3,4-dimethylisoxazolyl)] p-benzenesulfonamido |
| 3c. | N-[2-(4,6-dimethylpyrimidinyl)] p-benzenesulfonamido |
| 6c. | N-[2-(4,6-dimethylpyrimidinyl)] p-benzenesulfonamido |
| 3d. | N-[4-(2,6-dimethylpyrimidinyl)] p-benzenesulfonamido |
| 6d. | N-[4-(2,6-dimethylpyrimidinyl)] p-benzenesulfonamido |
| 3e. | N-[2-(5-methyl-1,3,4-thiadiazolyl)] p-benzenesulfonamido |

TABLE 1-continued

The following compounds are represented by the formula:

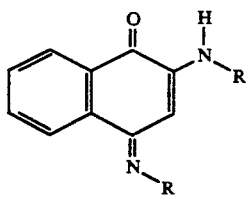

| Compound | R |
|---|---|
| 6e. | N-[2-(5-methyl-1,3,4-thiadiazolyl)] p-benzenesulfonamido |
| 3f. | N-[2-(4-methylpyrimidinyl)] p-benzenesulfonamido |
| 6f. | N-[2-(4-methylpyrimidinyl)] p-benzenesulfonamido |
| 3g. | N-[4-(2,6-dimethoxypyrimidinyl)] p-benzenesulfonamido |
| 6g. | N-[4-(2,6-dimethoxypyrimidinyl)] p-benzenesulfonamido |
| 3h. | N-[2-(5-methoxypyrimidinyl)] p-benzenesulfonamido |
| 6h. | N-[2-(5-methoxypyrimidinyl)] p-benzenesulfonamido |
| 3i. | N-(2-pyridinyl) p-benzenesulfonamido |
| 6i. | N-(2-pyridinyl) p-benzenesulfonamido |
| 3j. | N-[3-(6-methoxypyridazinyl)] p-benzenesulfonamido |
| 6j. | N-[3-(6-methoxypyridazinyl)] p-benzenesulfonamido |
| 3k. | N-(2-pyrimidinyl) p-benzenesulfonamido |
| 6k. | N-(2-pyrimidinyl) p-benzenesulfonamido |
| 3l. | N-[3-(5-chloropyridazinyl)] p-benzenesulfonamido |
| 6l. | N-[3-(5-chloropyridazinyl)] p-benzenesulfonamido |
| 3m. | N-(2-quinoxalinoyl) p-benzenesulfonamido |
| 6m. | N-(2-quinoxalinoyl) p-benzenesulfonamido |
| 3n. | N-[2-pyridinylmethyl] p-benzenesulfonamido |
| 6n. | N-[2-pyridinylmethyl] p-benzenesulfonamido |
| 3o. | N-hexadecyl p-benzenesulfonamido |
| 6o. | N-hexadecyl p-benzenesulfonamido |
| 3p. | N-[2-(4,6-dimethylpyrimidinyl)] m-benzenesulfonamido |
| 3q. | N-[2-(4,6-dimethylpyrimidinyl)] o-benzenesulfonamido |
| 3r. | N-[2-(4,6-dimethylpyrimidinyl)] 3-(6-methylbenzenesulfonamido) |
| 3s. | N-[2-(4,6-dimethylpyrimidinyl)] 4-(3-chlorobenzenesulfonamido) |
| 3t. | N-[2-(4,6-dimethylpyrimidinyl)]4-(3-chloro-2-thiophenyl-4-sulfonamido) |
| 3u. | N-[2-(4,6-dimethylpyrimidinyl)]4-(3-pyridinylsulfonamido) |
| 3v. | N-[2-(4,6-dimethylpyrimidinyl)] 3-(2,4,5-thiadiadiazolylsulfonamido) |
| 3w. | N-[2-(4,6-dimethylpyrimidinyl)]ethenyl-2-sulfonamido |
| 3x. | N-[2-(4,6-dimethylpyrimidinyl)] 1,3-butadienyl-4-sulfonamido |
| 3y. | N-[2-(4,6-dimethylpyrimidinyl)] naphthyl-4-sulfonamido |
| 3z. | N-[2-(4,6-dimethylpyrimidinyl)] 2-quinolinoyl-4-sulfonamido |
| 3aa. | N-[2-(4,6-dimethylpyrimidinyl)] 6-quinolinoyl-4-sulfonamido |
| 3ab. | amidino p-benzenesulfonamido |
| 3ac. | N-[N'-[2-(5-nitropyridinyl)]]-2-aminoethyl p-benzenesulfonamide |
| 3ad. | p-benzenesulfonamido |
| 3ae. | N-[2-(4,6-dimethylpyridinyl)] m-benezesulfonamido |
| 6ae. | N-[2-(4,6-dimethylpyridinyl)] m-benezesulfonamido |
| 3af. | N-[5-(1,3-dimethoxyphenyl)] p-benezesulfonamido |
| 6af. | N-[5-(1,3-dimethoxyphenyl)] p-benezesulfonamido |
| 3ag. | N-[2-(4,6-dimethylpyridinyl)]3-(6-methylbenzenesulfonamido) |
| 6ag. | N-[2-(4,6-dimethylpyridinyl)]3-(6-methylbenzenesulfonamido) |
| 3ah. | N-[2-(4,6-dimethylpyridinyl)] p-benzamido |
| 3ai. | N-[2-(4,6-dimethylpyrimidinyl)] p-benzamido |
| 3aj. | N-[2-(4,6-dimethylpyridinyl)] p-benzenesulfonamido |
| 3ak. | N-[3-(2-carbomethyoxythiophenyl)] p-benzenesulfonamido |

TABLE 2

| Compound | Salt | Recrystallization solvent(s) | Melting point °C. |
|---|---|---|---|
| 3a. | | methanol | 242-244 |
| 6a. | Sodium | | 265(dec) |
| 3b. | | methanol | 219-220 |
| 6b. | Sodium | | 255-258 |
| 3c. | | methanol | 256(dec) |
| 6c. | Sodium | | +350 |
| 3d. | | 1:1 THF:water | 189(dec) |
| 6d. | Sodium | | 254(dec) |
| 3e. | | methanol | 303-305 |
| 6e. | Sodium | | 258(dec) |
| 3f. | | 1:3 THF:methanol | 270-273 |
| 6f. | Sodium | | +305 |
| 3g. | | 1:10 THF:methanol | 220(dec) |
| 6g. | Sodium | | 300(dec) |
| 3h. | | methanol | 285-288 |
| 6h. | Sodium | | >305 |
| 3i. | | chloroform | 282-284 |
| 6i. | Sodium | | +300 |
| 3j. | | | 178-181 |
| 6j. | Sodium | | 266(dec) |
| 3k. | | THF | 284(dec) |
| 6k. | Sodium | | +300 |
| 3l. | | methanol | 234 |
| 6l. | Sodium | | +300 |
| 3m. | | methanol | 265(dec) |
| 6m. | Sodium | | |
| 3n. | | methanol | 178-180 |
| 6n. | Sodium | | 208(dec) |
| 3o. | | methylene chloride | 182-185 |
| 6o. | Sodium | | 182(dec) |
| 3ab. | | | 319-321 |
| 3ac. | | | 218-221 |
| 3ad. | | | 298-300 |
| 3ae. | | methanol | 160-162 |
| 6ae. | Sodium | | >300 |
| 3af. | | | 182-184 |
| 6af. | Sodium | | 285-288 |
| 3ag. | | 95% ethanol | 240-242 |
| 6ag. | Sodium | | 240(dec) |
| 3ah. | | 95% ethanol | 258-260 |
| 3ai. | | tetrahydrofuran | 269-272(dec) |
| aj. | | methanol | 135-137 |
| ak. | | chloroform | >300 |

Preferred compounds include compounds: 3a, 3b, 3c, 3d, 33, 3f, 3g, 3h, 3i, 3j, 3k, 3l, 3m, 3n, 3o, 3ab, 3ac, 3ad, 3ae, 3af, 3ag, 3ah, 3ai, 3aj, and 3ak. Of these, the more preferred compounds are: 3a, 3c, 3g, 3h, 3i, 3j, 3m, 3n, 3ac, 3ae, 3af, 3ag, 3ah, 3ai. Most preferred compounds include: 3c, 3i, 3m, 3n, 3ac, 3ae, 3af, 3ag, and 3ai.

EXAMPLE 2

4-[N,N''-(4-Amino-1-Imino-2-Oxo-1,2-Dihydronaphthyl)]-Bis[N-[3-(5-Methylisoxazolyl)]Benzenesulfonamide](Compound 3a)

To 1,2-napthoquinone-4-sulfonic acid potassium salt partially dissolved in anhydrous dimethyl sulfoxide (20 ml) under an atmosphere of nitrogen was added sulfamethoxazole (2.18 g, 9.61 mmol). After stirring 3h the reaction mixture was quenched with distilled water (50 ml). Collected the solid by suction filtration. Recrystallization of the solid from methanol provided an orange solid of the title compound (191 g, 31%), mp 242°-244° C. $^1$H NMR (DMSO-$d_6$) d 11.39 (br s, 2H), 9.29 (s, 1H), 8.39 (d, 1H, J=8Hz), 8.16 (d, 1H, J=8Hz), 7.76-7.91 (m, 4H), 7.72 (d, 2H, J=9Hz), 7.42 (d, 2H, J=9Hz), 7.18 (d, 2H, J=8.5Hz), 6.49 (s, 1H), 6.13 (s, 1H), 6.10 (s, 1H), 2.28 (s, 6H); IR KBr (disc) 3325, 3088, 2924, 2855, 1665, 1616, 1588, 1553, 1520, 1468, 1404, 1339, 1310, 1260, 1167, 1094, 723, 610 cm$^{-1}$. Anal. Calcd for $C_{30}H_{24}N_6O_7S_2$: C, 55.89; H, 3.75; N, 13.04; S, 9.94. Found: C, 56.01; H, 3.75; N, 12.94; S, 9.98.

EXAMPLE 3

Disodium 4-(N',N''-(4-Amino-1-Imino-2-Oxo-1,2-Dihydronaphthyl)]-Bis[N-(3-[-Methyl-Isoxazoyl)]Benzenesulfonamide (Compound 6a)

To 4-[N,N''-(4-Amino-1-imino-2-oxo-1,2-dihydronaphthyl)]—bis[N-(3-[-methyl-isoxazoy)]benzenesulfonamide (300 mg, 0.465 mmol, 3a) partially dissolved in methanol (35 ml) was added a solution of sodium hydroxide (37.2 g, 9.30 mmol) in distilled water (2 ml). A clear dark red solution was obtained with heating. The volatiles were removed under reduced pressure and oven drying of the residue at 105° C. under full vacuum yielded a garnet red solid of the title compound (318 mg, quantitative yield), mp 265° C. (dec). $^1$H NMR (DMSO-d$_6$) d 8.90 (s, 1H), 8.42 (d, 1H, J=8 Hz), 8.15 (d, 1H, J=8 Hz), 7.85 (t, 1H, J=8 Hz), 7.68-7.89 (m, 3H), 7.56 (d, 2H, J=8 Hz), 7.22 (d, 2H, J=8 Hz), 6.96 (d, 2H, J=8 Hz), 6.59 (s, 1H), 5.80 (s, 1H), 5.76 (s, 1H), 2.12 (s, 3H), 2.12 (s, 3H), IR KBr (disc) 3200, 2926, 1661, 1615, 1588, 1520, 1468, 1410, 1341, 1306, 1236, 1163, 1130, 1096, 1049, 945, 831, 754, 642, 611 cm$^{-1}$. Anal. calcd. for C$_{30}$N$_{22}$N$_6$O$_7$S$_2$Na.$\frac{1}{2}$H$_2$O:C, 51.65; H, 3.32; N, 12.05; S, 9.19; Na, 6.59. Found: C, 51.35; H, 3.43, N, 11.92; S, 9.05; Na, 6.48.

EXAMPLE 4

Protein Kinase C Inhibition

A protein kinase C (PKC) assay is designed to duplicate the in vivo conditions required for protein kinase C function. Therefore, pH, salt and cofactor concentrations are similar to physiologic levels. Either lysine rich histone H1 (H1) or Myelin basic protein (Mbp) are used in the assay as the phosphorylation acceptor-protein because they are readily available and serve as good substrates for protein kinase C. Enzyme was prepared from baculovirus-insect cell expression systems.

In the screening assay, phosphatidylserine (PS) and DAG were co-sonicated to form unilamellar and multilamellar vesicles. The concentration of lipids in the assay were suboptimal to maximize the detection potential of the assay for inhibitors or activators. Potential effector compounds were added to the assay in dimethylsulfoxide at four concentrations to give final inhibitor concentrations of 1, 10, 50, and 150 µM, respectively.

The assay was started with the addition of enzyme and stopped after 10 min by the addition of 25% trichloroacetic acid (TCA) and 1.0 mg/ml bovine serum albumin (BSA). The radioactive histone product was retained and washed on glass fiber filters that allow the unreacted P-ATP to pass through. The amount of phosphorylation was determined by measuring radioactivity with a scintillation counter. Controls were included in every assay to measure background activity in the absence of enzyme, activity in the absence of lipids, and the maximum enzyme activity with saturating levels of the activator lipids. Table 3 shows the protein kinase C assay components and their concentrations.

TABLE 3

| Assay Component | Concentration |
| --- | --- |
| HEPES pH 7.5 | 20 mM |
| MgCl$_2$ | 10 mM |
| CaCl$_2$ or EGTA | 940 µM (CaCl$_2$) or 100 µM (EGTA) |
| EGTA | 1 mM |
| Histone H1 (H1) or Myelin | 200 µg/ml (H1) or 750 mg/ml |

TABLE 3-continued

| Assay Component | Concentration |
| --- | --- |
| basic protein (Mbp) | |
| Phosphatidylserine | 120 µg/ml |
| Diacylglycerol | 2.0 µg/ml |
| Protein Kinase C | 0.6 µg/ml |
| g-$^{32}$P-ATP | 30 µM |

HEPES is N-[2-hydroxyethyl] piperazine-N'-[ethanesulfonic acid] and EGTA is Ethylene-bis (oxyethylenenitrilo) tetracetic acid.

Results of the protein kinase C assay are shown in Table 4 in columns labeled α, $β_{II}$, γ, δ, ε, and ζ which represent various PKC isoenzymes. Results are show as IC$_{50}$, which is the concentration of test compound needed to inhibit 50% of the protein kinase C activity in controls. Compounds of the present invention were able to effectively inhibit protein kinase activity.

TABLE 4

| Compound | IC$_{50}$ (µM) PKC isoenzymes | | | | | | PKA |
| --- | --- | --- | --- | --- | --- | --- | --- |
| | α | $β_{II}$ | γ | δ | ε | ζ | |
| 3a | 42 | 6 | 20 | 33 | 81 | | 114 |
| 6a | 42 | 24 | 20 | 34 | 145 | | 157 |
| 3b | 30 | 29 | 25 | 31 | 143 | | >150 |
| 6b | 35 | 50 | 29 | 39 | >150 | | >150 |
| 3c | 17 | 7 | 21 | 72 | >150 | | >150 |
| 6c | 7 | 14 | 7 | 10 | 15 | 132 | 48 |
| 3d | 37 | 31 | 36 | 95 | >150 | | >150 |
| 6d | 41 | 39 | 24 | 47 | >150 | | >150 |
| 3e | 17 | 14 | 22 | 43 | >150 | | 55 |
| 6e | 109 | 24 | 12 | 35 | >150 | 20 | 45 |
| 3f | 28 | 23 | 29 | 86 | >150 | | 48 |
| 6f | 24 | 23 | 18 | 43 | >150 | 35 | 46 |
| 3g | 32 | 25 | 14 | 40 | >150 | | >150 |
| 6g | 61 | 33 | 20 | >150 | >150 | 28 | 47 |
| 3h | 105 | 53 | 55 | 58 | >150 | | >150 |
| 6h | 108 | 97 | 41 | >150 | >150 | 47 | >150 |
| 3i | 23 | 26 | 15 | 37 | >150 | >150 | >150 |
| 6i | 14 | 47 | 10 | 120 | >150 | >150 | >150 |
| 3j | 67 | 45 | 15 | 17 | >150 | >150 | >150 |
| 6j | 106 | 47 | 30 | 113 | >150 | 49 | >150 |
| 3k | 113 | >150 | 24 | >150 | >150 | 37 | 111 |
| 6k | 116 | >150 | 16 | >150 | >150 | 35 | 111 |
| 3l | 27 | 24 | 7 | 78 | >150 | 28 | 98 |
| 6l | 44 | 29 | 9 | 50 | >150 | 9 | 89 |
| 3m | 8 | 22 | 14 | 122 | >150 | 28 | 82 |
| 6m | 9 | 23 | 10 | 37 | 141 | 9 | 145 |
| 3n | 75 | 141 | 24 | >150 | >150 | >150 | >150 |
| 6n | 134 | >150 | 44 | >150 | 149 | >150 | >150 |
| 3o | 117 | 138 | 118 | 139 | >150 | 26 | >150 |
| 6o | 100 | 99 | 94 | 102 | >150 | >150 | |
| 3ab | 125 | >150 | 76 | >150 | >150 | >150 | |
| 3ac | 85 | 89 | 22 | 147 | >150 | >150 | >150 |
| 3ae | 31 | 52 | 16 | 85 | >150 | >150 | >150 |
| 6ae | | | | | | | |
| 3af | 102 | 143 | 40 | >150 | 111 | >150 | 62 |
| 6af | 113 | >150 | 60 | >150 | >150 | >150 | |
| 3ag | 7 | 17 | 20 | 30 | 8 | 28 | >150 |
| 6ag | 22 | 28 | 16 | 49 | 35 | >150 | |
| 3ah | 136 | 145 | 70 | >150 | >150 | >150 | |
| 3ai | 56 | 101 | 9 | >150 | >105 | >150 | >150 |
| 3aj | 90 | >150 | 88 | >150 | >150 | >150 | |

EXAMPLE 6 cAMP Dependent Protein Kinase (PKA) Assay

Compounds found to be inhibitors of protein kinase C were tested for inhibitory activity against cAMP dependent protein kinase (PKA). This enzyme, like protein kinase C, plays an important role in cell-cell communication and is activated by a second messenger, cAMP. Secondary screening against PKA is useful for ascertaining the selectivity of the compounds of the invention. The standard assay conditions are given in Table 5.

The catalytic subunit of PKA (Sigma Chemical Company, St. Louis, Mo.) was mixed with buffer before addition of the inhibitor in dimethylsulfoxide (DMSO). Potential inhibitor compounds were added to the assay in dimethylsulfoxide at two concentrations to give final inhibitor concentrations of 30 and 150 μM, respectively. The assay was started by the addition of $^{32}$P-ATP and the reaction was allowed to proceed for 10 min before stopping with 25% trichloroacetic acid (TCA) and 1.0 mg/ml bovine serum albumin (BSA). Phosphorylated protein was then isolated by filtration and the radioactivity was counted by a beta scintillation counter.

TABLE 5

| Assay Components | Concentration |
|---|---|
| HEPES pH 7.5 | 20 μM |
| Histone H1 | 200 μg/ml |
| Dithiothreitol | 32 μg/ml |
| Protein Kinase A | 2.6 μg/ml |
| g$^{32}$ ATP | 30 μM |

The results of the cAMP dependent protein kinase activity assay are reported in Table 4. Compounds 3b, 6b, 3c, 3d, 6d, g, 3h, 6h, 3i, 6i, 3j, 6j, 3n, 6n, 3o, 3ac, 3ae, 3ag, 6ag and 3ai did not effect on PKA activity. Thus, those compounds are selective for protein kinase C, and have no effect on cAMP dependent protein kinase. Such compounds should have no effect on the metabolic pathways associated with stimulation of protein kinase by cAMP and are, accordingly, preferred.

EXAMPLE 7

Human Tumor Cell Growth Inhibition

MCF-7 a human breast tumor cell line was obtained from the National Cancer Institute, Frederick, Md. Tumor cells were trypsinized with 0.05% trypsin obtained from GIBCO (Grand Island Biological Co. Laboratories, Grand Island, N.Y.), counted with a hemacytometer and seeded at a concentration of 7,500 cells/well in a 96 well microtiter plate and allowed to attach to the surface overnight. To determine a concentration response, test agents were serially diluted an 100 ml/well added at 2× final concentration to quadruplicate cultures to bring the total volume of each well to 200 ml. The microtiter plate was then incubated at 37° C., 5% CO$_2$ for 24 hrs with $^3$H-thymidine added at a concentration of 0.5 mCi/well in 50 ml of 0.05% trypsin (GIBCO) was added to each well. Cells were checked microscopically to determine detachment from surfaces, and plates were harvested with a cell harvester (PHD, Cambridge Technology, Inc.). Filter paper corresponding to wells were placed in scintillation vials and counted to determine the amount $^3$H-thymidine incorporated by the cells. Counts per minute (CPM) of quadruplicate cultures were averaged and a percent of control calculated for each test agent concentration by the following formula:

$$\% \text{ Control} = \frac{\text{Mean CPM test agent}}{\text{Mean CPM control (media only)}} \times 100$$

The IC$_{50}$ or concentration necessary to inhibit the proliferation of cells by 50% compared to control, of each test agent was determined by plotting % control vs log concentration for each dilution and then linear forecasting the 50% control value onto the X axis on a Quattro Pro computer program. Only regression values with a correlation coefficient greater then 0.9 were considered acceptable.

As shown in Table 6, compounds of the invention were able to inhibit $^3$H-thymidine uptake and thus inhibit the proliferation of the tested cell lines.

TABLE 6

| | IC$_{50}$ (μM) |
|---|---|
| Compound | MCF-7 |
| 3a | 13.30 |
| 3c | 7.03 |
| 6c | 15.50 |
| 3d | 17.20 |
| 6d | 17.9 |
| 3f | 16.60 |
| 6f | 17.7 |
| 3g | 16.50 |
| 6g | 21.0 |
| 3h | 12.20 |
| 6h | 14.9 |
| 3i | 13.8 |
| 6i | 20.0 |
| 3j | 16.1 |
| 6j | 10.9 |
| 3m | 17.9 |
| 6m | 19.0 |
| 3n | 1.02 |
| 6n | 0.75 |
| 3ac | 0.16 |
| 3ae | 4.80 |
| 6ae | |
| 3af | 0.83 |
| 6af | 1.20 |
| 3ag | 2.40 |
| 6ag | 1.80 |
| 3ah | 1.40 |
| 3ai | 0.03 |

EXAMPLE 8

Human Keratinocyte Inhibition

Materials and Methods

Proliferating normal human epidermal keratinocyte (NHEK) cells were obtained in the second passage and grown in keratinocyte growth medium, KGM (Clonetics, Inc.) at 37° C., 5% CO$_2$. The cells were trypsinized (0.25%), centrifuged, counted with a hemocytometer, and seeded at a concentration of 5000 cells in 100 μl well in a 96-well microtiter plate.

After the cells were allowed to attach to the microtiter plate overnight, test agents were titrated to determine the dose response. This was done by adding each test agent dilution in quadruplicate to the plate at 2× final concentration in 100 μl to bring the total volume of each well to 200 μl. Culture media with no test agent added was used as a normal control. Duplicate sets of plates were established.

$^3$H TdR Assay

After twenty-four hours of incubation with test compounds 37° C. and 5% CO$_2$, 50 ml of 0.01 mCi/ml tritiated thymidine (New England Nuclear) was added to each well and allowed to incubate for another 4 hours under the same conditions.

Supernatant was aspirated and discarded and 50 ml of 0.05% trypsin (Gibco) was added to each cell. Cells were checked microscopically to determine detachment from surfaces and then harvested onto glass filters. The filters were then placed in vials to which scintillant was added and counted for one minute each in a scintillation counter.

Calculations

Determine mean cpm of wells containing test agent (n=4) or KGM control (n=16). Calculate % of control by the formula:

$$\% \text{ Control} = \frac{\text{Mean test agent (cpm)}}{\text{Mean control (cpm)}} \times 100$$

The $IC_{50}$, or connection necessary to inhibit 50% of control, of each test agent was determined by plotting % control vs log concentration for each dilution and then linear forecasting the 50% control value onto the X axis on a Quatro Pro computer program. Only regression values with a correlation coefficient greater than 0.9 were considered acceptable.

Reference Standards

The reference standard used was sphingosine. The $IC_{50}$ range obtained is as follows:

|  | $^3$HTdR |
|---|---|
| Sphingosine | 4–11 μM |

The results shown in Table 7 indicate that the compounds of the invention were good inhibitors of human keratinocyte proliferation yet not cytotoxic to the cells and thus will be useful in treating topical inflammatory conditions such as psoriasis and other conditions where hyperproliferation of keratinocytes is a symptom.

TABLE 7

| Compound | $IC_{50}$ (μM) NHEK |
|---|---|
| 3a | 0.54 |
| 6a | 1.20 |
| 3b | 11.60 |
| 6b | 16.70 |
| 3c | 0.52 |
| 6c | 0.04 |
| 3d | 2.00 |
| 6d | 2.50 |
| 3e | 8.70 |
| 6e | 8.60 |
| 3f | 1.20 |
| 6f | 1.40 |
| 3g | 0.60 |
| 6g | 1.40 |
| 3h | 0.90 |
| 6h | 1.20 |
| 3i | 0.61 |
| 6i | 7.30 |
| 3j | 0.34 |
| 6j | 0.82 |
| 3k | 1.80 |
| 6k | 1.80 |
| 3l | 4.30 |
| 6l | 3.30 |
| 3m | 0.40 |
| 6m | <0.39 |
| 3n | 1.10 |
| 6n | 0.50 |
| 3o | 3.80 |
| 3ac | 0.08 |
| 3ae | <0.39 |
| 6ae | |
| 3af | <0.39 |
| 3ag | |
| 6ag | 0.50 |
| 3ah | 1.40 |
| 3ai | 0.16 |

EXAMPLE 9

Neutrophil Superoxide Anion ($O_2$) Release Assay

Phorbol-12,13-myristate acetate (PMA) stimulates $O_2$ production in human neutrophils which in turn reduces cytochrome C. Reducing cytochrome C increases absorbance and the change in optical density (OD) is proportional to the amount of $O_2$ produced by PMA stimulation. Inhibition is expressed as an $IC_{50}$ value and is the amount of test compound that will inhibit fifty percent of the PMA-stimulated respiratory outburst, i.e. $O_2^{31}$ production (Lherer et al. (1981) J. Clinical Invest. 68:1314; Roberts et al. (1982) J. Immunological Methods 49:193).

Human donor blood in 0.38% Sodium Citrate was centrifuged for 10 minutes at 160 ×g at room temperature. Platelet-rich plasma was removed leaving the buffy coat and the red cell-enriched fraction. Saline with 0.38% Sodium Citrate was added to this fraction up to the original blood volume. The enriched blood sample was diluted 1:1 (v:v) with 3% dextran T500 (Pharmacia) in normal saline and placed in a 60 cc syringe, inverted over a beaker and allowed to settle 30 minutes at room temperature.

Leukocyte-enriched plasma was removed from the syringe, placed into 50 ml polypropylene conical centrifuge tubes and underlaid with 15–20 ml Lymphocyte Separation Medium (LSM Organon Technica). The tubes were centrifuged for 40 minutes at 500×g at room temperature. The plasma, buffy coat and LSM were aspirated off the pellets which contained red blood cells and neutrophils.

The pellets were vortexed and 10 ml ice-cold 0.2% NaCl was added to lyse the red blood cells while vortexing again for 10 seconds. Ice-cold 1.6% NaCl was added while vortexing for 10 seconds. The cells were combined from multiple tubes, centrifuged 10 min at 400×g at 4° C. This red cell lysis was repeated and the resulting neutrophil pellet was washed once in Reaction HBSS (GIBCO, HBSS with $Ca^{++}$ and $Mg^{++}$.238% HEPES, 0.1% dextrose, 0.1% RIA grade bovine serum albumin, PH 7.2). The cells were resuspended in 1/5 the original blood volume with Reaction HBSS, counted and adjusted to $4.0 \times 10^6$ cells/ml at 4° C.

PMA Dose Response on Isolated Neutrophils

Duplicate samples of neutrophils were tested in 12×75 mm polypropylene tubes containing 0.25 ml of the neutrophil suspension. Cytochrome C mix (0.25 ml, 6.0 mg/ml cytochrome C type IV (Sigma) plus 1200 U/ml bovine liver catalase (Sigma) in Reaction HBSS described above) was added. PMA was added at 2× the final concentration in 0.5 ml of Reaction HBSS. PMA final test concentration were 0.0, 0.3, 9.0, 27.0, and 81.0 ng/ml. The tubes were vortexed and incubated for 10 minutes at 37° C. with shaking. After chilling for 5 minutes at 4° C. and centrifuging for 10 minutes at 4° C., 550×g, 0.5 ml of supernatant was removed from each tube. Normal saline (0.5 ml) was added to each 0.5 ml sample of supernatant and the absorbance of each sample was read at 550 nm on a spectrophotometer (Shimadzu). The PMA concentration which gives nearly maximal stimulation of superoxide release was determined.

Direct Assay of Test Agent on Neutrophil $O_2$ Release

The test samples of neutrophils were prepared as in the PMA dose response through addition of cytochrome C mix. Then 0.4 ml of Reaction HBSS as a control or test agent at 2.5×final test concentration was added and the tubes were vortexed and incubated for 30 minutes at 37° C. with shaking. PMA (0.1 ml) was added at a 10× concentration of the final concentration determined above. The samples were incubated for 10 minutes at 37° C. with shaking, chilled for 5 minutes at 4° C., and then centrifuged for 5 minutes at 550×g at 4° C. The supernatant (0.5 ml) was diluted with 0.5 ml normal saline as above and the absorbance was then determined at 550 nm. The percent change was calculated as follows:

$(x - BKG)$ = (mean of $A_{550}$ values − mean of Reaction HBSS background $A_{550}$ values)

% Change = $\frac{(x - BKG) \text{ of test agent}}{(x - BKG) \text{ of control}} - 1 \times 100$ D-sphingosine (Sigma) used as reference standard.

Results

Human neutrophils were first isolated according to Lherer et al. ((1981) J. Clinical Invest. 68:1314) and then tested for stimulation of superoxide anion release with phorbol--12,13-myristate acetate (PMA) in a dose-dependent manner. A PMA concentration was then determined for that donor sample providing a dose for testing the inhibitors.

The $IC_{50}$ values of the tested compounds that were able to inhibit $O_2^{31}$ production by PMA-stimulated neutrophils are shown in Table 8. In addition, the known PKC inhibitor, D-sphingosine, which is also known to inhibit neutrophil oxidative burst (Wilson, et al, (1986) J. Biol. Chem. 261:12616) was shown to have a comparable $IC_{50}$ value of 2.85 μM in this test system.

TABLE 8

| Neutrophil Superoxide Release | |
|---|---|
| Compound | $IC_{50}$ (μM) |
| 3a | 8.90 |
| 6a | 8.00 |
| 3b | 7.60 |
| 3c | 0.77 |
| 6c | 1.88 |
| 3d | 5.85 |
| 6d | 6.47 |
| 3e | 8.38 |
| 6e | 4.78 |
| 3f | 2.51 |
| 6f | 2.11 |
| 3g | 2.75 |
| 6g | 1.34 |
| 3h | 8.70 |
| 6h | 2.40 |
| 3i | 0.10 |
| 6i | 0.11 |
| 3j | 1.74 |
| 6j | 3.33 |
| 6k | 6.83 |
| 3l | 0.90 |
| 6l | 5.23 |
| 3m | 1.31 |
| 6m | 1.39 |
| 3n | 0.22 |
| 6n | 0.10 |
| 3ac | 0.05 |
| 3ae | 0.04 |
| 6ae | |
| 3af | 0.06 |

TABLE 8-continued

| Neutrophil Superoxide Release | |
|---|---|
| Compound | $IC_{50}$ (μM) |
| 6af | 0.07 |
| 3ag | 0.04 |
| 6ag | 0.06 |
| 3ah | 8.97 |
| 3ai | 4.02 |

I claim:

1. A compound having the formula:

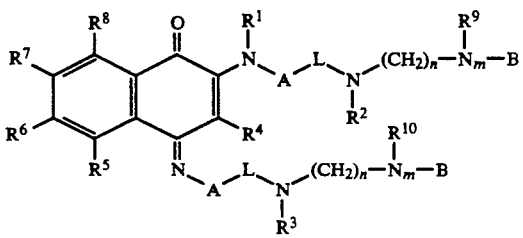

wherein:
a is: a phenyl or naphthyl ring system;
L is: $SO_2$ CO;
$R^1$–$R^3$ are each, independently: hydrogen, alkyl, aryl, alkylaryl, arylalkyl, or cycloalkyl;
$R^4$–$R^8$ are each, independently: hydrogen, alkyl, aryl, alkylaryl, arylalkyl, halogen, nitro, amino, acylamino, hydroxy, carboxyl, alkoxy, aryloxy, thioalkoxyl, alkylthio, arylthio or a fused aromatic ring;
B is: hydrogen, aryl, arylalkyl, alkylaryl, $C_3$-$C_8$ cycloalkyl; $C_2$-$C_{20}$ alkyl, $C_2$-$C_{20}$ alkenyl, $C_2$-$C_{20}$ alkynyl, acyl or substituted thereof; or pyrrolyl, imidazolyl, triazolyl, tetrazolyl, furanyl, thiophenyl, isoxazolyl, isothiazolyl, oxazolyl, 1,2,4-thiadiazolyl, pyridazinyl, pyridinyl, pyrimidinyl, pyrazinyl, quinoxalinyl, quinolinyl, isoquinolinyl, wherein all rings may be substituted;
m is: 0–1; and
n is: 0–6;
wherein when m is 1,
$R^9$ and $R^{10}$ are each, independently: hydrogen, alkyl, aryl, alkylaryl, arylalkyl or cycloalkyl groups;
or pharmaceutically acceptable salts of said compound.

2. The compound of claim 1 wherein $R^1$-$R^8$ are each, independently, hydrogen or lower alkyl, aryl, alkylaryl or arylalkyl groups of $C^1$-$C_{20}$.

3. The compound of claim 1 wherein $R^1$-$R^8$ are each hydrogen.

4. The compound of claim 1 wherein A is: phenyl, methyl-m-phenyl, chloro-p-phenyl or naphthyl.

5. The compound of claim 1 wherein A is: p-phenyl; m-phenyl; or 3-(6-methylphenyl).

6. The compound of claim 1 wherein A is p-phenyl.

7. The compound of claim 1 wherein B is: 3-(5-methylisoxazolyl); 5-(3,4-dimethylisoxazolyl); 2-(4,6-dimethylpyrimidinyl); 4-(2,6-dimethylpyrimidinyl);2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 3-(6-chloropyridazinyl); 2-quinoxalinoyl; hexadecyl; amidino; 2-(5-nitropyridinyl); hydrogen; 2-(4,6-dimethylpyridinyl); 5-(1,3 dimethoxyphenyl); or 3-(2-carbomethoxythiophenyl).

8. The compound of claim 1 wherein B is: 3-(5-methylisoxazolyl); 2-(4,6-dimethylpyrimidinyl); 4-(2,6-dimethoxypyrimidinyl); 2-(5-methoxypyrimidinyl); 2-pyridinyl; 3-(6-methoxypyridazinyl); 2-quinoxalinoyl; 2-(5-nitropyridinyl); 2-(4-6 dimethylpyridinyl); or 5-(1,3 dimethoxyphenyl).

9. The compound of claim 1 wherein B is: 2-(4,6-dimethylpyrimidinyl); 2-pyridinyl; 2-quinoxalinoyl; 2-(5-nitropyridinyl); 2-(4-6 dimethylpyridinyl); or 5-(1,3 dimethoxyphenyl).

10. The compound of claim 1 wherein B is: 2-(4,6-dimethylpyrimidinyl).

11. The compound of claim 1 wherein L is $SO_2$.

12. The compound of claim 1 wherein L is CO.

13. The compound of claim 1 wherein n is 0-3.

14. The compound of claim 1 wherein n is 0.

15. The compound of claim 1 wherein m is 0.

16. The compound of claim 1 wherein:
m is 1;
$R^9$ and $R^{10}$ are each, independently: hydrogen, $C_1$-$C_{20}$ alkyl, aryl, alkylaryl, arylalkyl or $C_3$-$C_{20}$ cycloalkyl.

17. The compound of claim 1 wherein:
m is 1; and,
$R^9$-$R^{10}$ are each hydrogen.

18. The compound of claim 1 wherein:
A is phenyl, 4-methyl-3-phenyl, 2-chloro-4-phenyl or 1,4-naphthyl;
L is $SO_2$ or CO;
n is 0-2; and
B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 2-quinoxalinoyl; hexadecyl; amidino; 2-(5-nitropyridinyl); hydrogen; 2-(4,6-dimethylpyridinyl); 5-(1,3-dimethoxyphenyl); 3-(2-carbomethoxythiophenyl); or 3-(6-chloropyridazinyl).

19. The compound of claim 1 wherein:
A is p-phenyl, m-phenyl, or 3-(6-methylphenyl);
L is $SO_2$ or CO;
n is 0-2; and
B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 3-(6-chloropyridazinyl); 2-quinoxalinoyl; hexadecyl; amidino; 2-(5-nitropyridinyl); hydrogen; 2-(4-6 dimethylpyridinyl); 5-(l,3 dimethoxyphenyl); or 3-(2-carbomethoxythiophenyl).

20. The compound of claim 1 wherein:
A is p-phenyl, L is $SO_2$, m is 0, n is 0 and B is 3-(5-methylisoxazolyl);
A is p-phenyl, L is $SO_2$, m is 0, n is 0 and B is 5-(3,4-dimethylisoxazolyl);
A is p-phenyl, L is $SO_2$, m is 0, n is 0 and B is 2-(4,6-dimethylpyrimidinyl);
A is p-phenyl, L is $SO_2$, m is 0,n is 0 and B is 4-(2,6-dimethylpyrimidinyl);
A is p-phenyl, L is $SO_2$, m is 0, n is 0 and B is 2-(5-methyl-1,3,4-thiadiazolyl);
A is p-phenyl, L is $SO_2$, m is 0, n is 0 and B is 2-(4-methylpyrimidinyl);
A is p-phenyl, L is $SO_2$, m is 0, n is 0 and B is 4-(2,6-dimethoxypyrimidinyl);
A is p-phenyl, L is $SO_2$, m is 0, n is 0 and B is 2-(5-methoxypyrimidinyl);
A is p-phenyl, L is $SO_2$, m is 0, n is 0 and B is 2-pyridinyl;
A is p-phenyl, L is $SO_2$, m is 0, n is 0 and B is 3-(6-methoxypyridazinyl);
A is p-phenyl, L is $SO_2$, m is 0, n is 0 and B is 2-pyrimidinyl;
A is p-phenyl, L is $SO_2$, m is 0, n is 0 and B is 3-(5-chloropyridazinyl);
A is p-phenyl, L is $SO_2$, m is 0, n is 0 and B is 2-quinoxalinoyl;
A is p-phenyl, L is $SO_2$, m is 0, n is 0 and B is hexadecyl;
A is m-phenyl, L is $SO_2$, m is 0, n is 0 and B is 2-(4,6-dimethylpyrimidinyl);
A is o-phenyl, L is $SO_2$, m is 0, n is 0 and B is 2-(4,6-dimethylpyrimidinyl);
A is 4-methyl-3-phenyl, L is $SO_2$, m is 0, n is 0 and B is 2-(4,6-dimethylpyrimidinyl);
A is 2-chloro-4-phenyl, L is $SO_2$, m is 0, n is 0 and B is 2-(4,6-dimethylpyrimidinyl);
A is naphthyl, L is $SO_2$, m is 0, n is 0 and B is 2-(4,6-dimethylpyrimidinyl);
A is p-phenyl, L is $SO_2$, m is 0, n is 1 and B is 2-pyridinyl;
A is p-phenyl, L is $SO_2$, m is 0, n is 0 and B is amidino;
A is p-phenyl, L is $SO_2$, m is 1, n is 2 and B is 2-(5-nitropyridinyl);
A is p-phenyl, L is $SO_2$, m is 0, n is 0 and B is hydrogen;
A is m-phenyl, L is $SO_2$, m is 0, n is 0 and B is 2-(4,6-dimethylpyridinyl);
A is p-phenyl, L is $SO_2$, m is 0, n is 0 and B is 5-(1,3-dimethoxyphenyl);
A is 3-(6-methylphenyl), L is $SO_2$, m is 0, n is 0 and B is 2-(4,6-dimethylpyridinyl);
A is p-phenyl, L is CO, m is 0, n is 0 and B is 2-(4,6-dimethylpyridinyl);
A is p-phenyl, L is CO, m is 0, n is 0 and B is 2-(4,6-dimethylpyridinyl); or
A is p-phenyl, L is $SO_2$, m is 0, n is 0 and B is 2-(4,6 dimethylpyridinyl); or
A is p-phenyl, L is $SO_2$, m is 0, n is 0 and B is 3-2-carbomethoxythiophenyl).

21. A method of inhibiting protein kinase C activity which comprises contacting protein kinase C with an effective amount of a compound of claim 1.

22. The method of claim 21 wherein:
A is a phenyl, 4-methyl-3-phenyl, 2-chloro-4-phenyl or 1,4-naphthyl;
L is $SO_2$ or CO;
n is 0-2; and
B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 2-quinoxalinoyl; hexadecyl; amidino; 2-(5-nitropyridinyl); hydrogen; 2-(4,6-dimethylpyridinyl); 5-(1,3-dimethoxyphenyl); 3-(2-carbomethoxythiophenyl); or 3-(6-chloropyridazinyl).

23. The method of claim 21 wherein:
A is p-phenyl, m-phenyl, or 3-(6-methylphenyl);
L is $SO_2$ or CO;

n is 0-2; and

B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 3-(6-chloropyridazinyl); 2-quinoxalinoyl; hexadecyl; amidino; 2-(5-nitropyridinyl); hydrogen; 2-(4,6-dimethylpyridinyl); 5-(1,3-dimethoxyphenyl); or 3-(2-carbomethoxythiophenyl).

24. A method of treating an animal suspected of experiencing inflammatory, cardiovascular and/or neoplastic diseases which comprises administering an effective amount of a compound of claim 1.

25. The method of claim 24 wherein:

A is phenyl, 4-methyl-3-phenyl, 2-chloro-4-phenyl or 1,4-naphthyl;

L is $SO_2$ or CO;

n is 0-2; and

B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 2-quinoxalinoyl; hexadecyl; amidino; 2-(5-nitropyridinyl); hydrogen 2-(4,6-dimethylpyridinyl); 5-(1,3-dimethoxyphenyl); 3-(2-carbomethoxythiophenyl); or 3-(6-chloropyridazinyl).

26. The method of claim 25 wherein:

A is p-phenyl, m-phenyl, or 3-(6-methylphenyl);

L is $SO_2$ or CO;

n is 0-2; and

B is 3-(5-methylisoxazolyl); 5-(3,4-dimethylisoxazolyl); 2-(4,6-dimethylpyrimidinyl); 4-(2,6-dimethylpyrimidinyl); 2-(5-methyl-1,3,4-thiadiazolyl); 2-(4-methylpyrimidinyl); 4-(2,6-dimethoxypyrimidinyl); 2-(5-methoxypyrimidinyl); 2-pyridinyl; 3-(6-methoxypyridazinyl); 2-pyrimidinyl; 3-(6-chloropyridazinyl); 2-quinoxalinoyl; hexadecyl; amidino; 2-(5-nitropyridinyl); hydrogen; 2-(4,6-dimethylpyridinyl); 5-(1,3 dimethoxyphenyl); or 3-(2-carbomethoxythiophenyl).

* * * * *